(12) United States Patent
Kulkarni

(10) Patent No.: US 10,518,071 B2
(45) Date of Patent: Dec. 31, 2019

(54) TRANSDERMAL MICRONEEDLE DRUG DELIVERY DEVICE AND METHOD

(71) Applicant: Gajanan Kulkarni, Toronto (CA)

(72) Inventor: Gajanan Kulkarni, Toronto (CA)

(73) Assignee: Gajanan Kulkarni, Toronto, Ontario (CA)

( * ) Notice: Subject to any disclaimer, the term of this patent is extended or adjusted under 35 U.S.C. 154(b) by 0 days.

(21) Appl. No.: 15/387,796

(22) Filed: Dec. 22, 2016

(65) Prior Publication Data

US 2017/0182300 A1    Jun. 29, 2017

Related U.S. Application Data

(60) Provisional application No. 62/272,320, filed on Dec. 29, 2015.

(51) Int. Cl.
*A61M 37/00* (2006.01)
*A61M 5/142* (2006.01)
*A61M 5/20* (2006.01)

(52) U.S. Cl.
CPC .... *A61M 37/0015* (2013.01); *A61M 5/14248* (2013.01); *A61M 5/20* (2013.01); *A61M 2005/14252* (2013.01); *A61M 2037/0023* (2013.01); *A61M 2037/0061* (2013.01); *A61M 2202/048* (2013.01); *A61M 2205/59* (2013.01)

(58) Field of Classification Search
CPC .......... A61M 37/0015; A61M 5/14248; A61M 5/20; A61M 2037/0023; A61M 2037/0061; A61M 2005/14252; A61M 2205/59; A61M 2202/048
See application file for complete search history.

(56) References Cited

U.S. PATENT DOCUMENTS

| | | | |
|---|---|---|---|
| 6,334,856 B1 | 1/2002 | Allen et al. | |
| 6,503,231 B1 | 1/2003 | Prausnitz et al. | |
| 6,611,707 B1 | 8/2003 | Prausnitz et al. | |
| 8,696,637 B2 | 4/2014 | Ross | |
| 2010/0121271 A1 | 5/2010 | Perriere et al. | |
| 2011/0172601 A1* | 7/2011 | Beebe | A61M 37/0015 604/131 |
| 2012/0109066 A1 | 5/2012 | Chase et al. | |
| 2012/0123387 A1* | 5/2012 | Gonzalez | A61M 37/0015 604/506 |
| 2012/0310169 A1 | 12/2012 | Sonderegger et al. | |

FOREIGN PATENT DOCUMENTS

| WO | WO 97/21457 | 12/1995 |
|---|---|---|
| WO | WO 2010/015770 | 2/2010 |
| WO | WO 2012/089627 | 7/2012 |

OTHER PUBLICATIONS

International Search Report corresponding to International Application No. PCT/CA2016/051529, dated Mar. 8, 2017, 6 pages.
Henry et al., "Micramachined Needles for the Transdermai Delivery of Drugs," *Micro Electra Mechanical Systems*, Heidelberg, Germany, (Jan. 26-29, 1998) pp. 494-498.

\* cited by examiner

*Primary Examiner* — Theodore J Stigell
(74) *Attorney, Agent, or Firm* — Myers Bigel, P.A.

(57) ABSTRACT

A transdermal drug delivery device comprises: a reservoir for holding a drug; and at least one microneedle in fluid communication with the reservoir through which the drug can be delivered transdermally, wherein the transdermal drug delivery device is concealed from view during operation thereof.

14 Claims, 19 Drawing Sheets

TRANSDERMAL MICRONEEDLE DRUG DELIVERY DEVICE AND METHOD

RELATED APPLICATIONS

This application claims the benefit of U.S. Provisional Application Ser. No. 62/272,320, filed Dec. 29, 2015, the disclosure of which is incorporated by reference in its entirety.

FIELD

The present invention relates to a drug delivery device. More specifically, the present invention is, in aspects, concerned a transdermal microneedle drug delivery device and related methods and uses.

BACKGROUND

Many medications need to be administered by needle, which can be a fearful experience for patients, particularly children. During certain medical or dental procedures, behaviour and anxiety can be managed through administration of such medications, however, the typical route of administration, namely by needle, can itself cause significant anxiety.

U.S. Pat. No. 8,696,637 describes a transdermal patch for delivering a controlled volume of a fluidic drug compound to skin. More particularly, the patch contains a microneedle assembly that is configured to be placed in fluid communication with a drug delivery assembly. The microneedle assembly contains a support and a plurality of microneedles that extend outwardly from the support. The microneedles are formed with one or more channels of a certain dimension such that passive capillary flow drives a flow of the drug compound. The drug delivery assembly contains a reservoir for the drug compound that is in fluid communication with a rate control membrane that helps control a flow rate of the drug compound by modulating the pressure of the drug compound, downstream from the reservoir. A release member is also positioned adjacent to the microneedle and drug delivery assemblies. Prior to use, the release member acts as a barrier to the flow of the drug compound and thus inhibits premature leakage. In this manner, the patch can initially be provided in an "inactive" configuration in which the drug compound is securely retained. When it is desired to release the drug compound, the patch can simply be activated by at least partially separating the release member from the drug delivery and microneedle assemblies.

U.S. Pat. No. 6,611,707 describes simple microneedle devices for delivery of drugs across or into biological tissue, which permit drug delivery at clinically relevant rates across or into skin or other tissue barriers, with minimal or no damage, pain, or irritation to the tissue. The devices include a substrate to which a plurality of hollow microneedles are attached or integrated, and at least one reservoir, containing the drug, selectably in communication with the microneedles, wherein the volume or amount of drug to be delivered can be selectively altered. The reservoir can be formed of a deformable, preferably elastic, material. The device typically includes a means, such as a plunger, for compressing the reservoir to drive the drug from the reservoir through the microneedles. In one embodiment, the reservoir is a syringe or pump connected to the substrate.

There is a need for alternative devices and methods to overcome or mitigate at least some of the deficiencies of the prior art.

SUMMARY

In accordance with an aspect, there is provided a transdermal drug delivery device comprising:
a reservoir for holding a drug; and
at least one microneedle in fluid communication with the reservoir through which the drug can be delivered transdermally,
wherein the transdermal drug delivery device is concealed from view during operation thereof.

In an aspect, the device further comprises a housing that surrounds the reservoir.

In an aspect, the reservoir is rigid.

In an aspect, depression of the reservoir delivers the drug through the at least one microneedle.

In an aspect, the device further comprises a plunger for delivering the drug from the reservoir through the at least one microneedle.

In an aspect, the plunger comprises a gasket.

In an aspect, the device further comprises a flange surrounding the periphery of the reservoir.

In an aspect, the flange comprises an adhesive for securing the drug delivery device such that the microneedles are facing the skin.

In an aspect, the device further comprising an outer covering enclosing the reservoir and/or the housing and leaving the microneedles exposed, wherein the outer covering resembles a bandage.

In an aspect, the outer covering comprises ornamentation.

In an aspect, the ornamentation is selected so as to appeal to a child.

In an aspect, the at least one microneedle is a plurality of microneedles.

In an aspect, the device further comprises a housing comprising an actuator for deploying the at least one microneedle.

In an aspect, the actuator is a button.

In an aspect, the device further comprises fastening elements attachable to the housing and configured for securing the transdermal delivery device to a wearer.

In an aspect, the fastening elements conceal the housing from the wearer.

In an aspect, fastening elements comprise ornamentation.

In an aspect, the ornamentation is selected so as to appeal to a child.

In an aspect, the device further comprises connecting tubing in fluid communication with the reservoir and the at least one microneedle.

In an aspect, the connecting tubing is flexible to allow for small movements between a first position before actuation of the at least one microneedle and a second position after actuation of the at least one microneedle.

In an aspect, the connecting tubing forms a substantially perpendicular connection with the reservoir and terminates in a substantially perpendicular intersecting portion of connecting tubing which engages with the at least one microneedle.

In an aspect, the device further comprises a finger rest area on a top casing of the housing.

In an aspect, the device is remotely operable.

In an aspect, the device is automated.

In an aspect, the device is operably connected to a portable base unit device.

In an aspect, the portable base unit delivers the drug and/or deploys the at least one microneedle.

In an aspect, the device contains a predetermined dose of the drug in the reservoir.

In an aspect, the reservoir holds more than one drug.

In an aspect, the device comprises more than one reservoir.

In an aspect, each reservoir comprises a different drug.

In an aspect, there are two reservoirs.

In an aspect, the device comprises a separate plunger for each reservoir.

In an aspect, the device comprises a single plunger for simultaneously delivering the drug from each.

In an aspect, the device further comprises an injection unit within the housing, wherein the injection unit comprising a bottom cap.

In an aspect, the bottom cap comprises a first indentation or void with a first position and a second indentation or void with a second position relative to the first position and wherein the first indentation or void lockingly engages one of a pair of protuberances on the actuator before actuation of the at least one microneedle and the second indentation or void lockingly engages with one of the pair of protuberances on the actuator after actuation of the at least one microneedle.

In an aspect, movement of the pair of protuberances before and after actuation alerts the user that the at least one microneedle has been ejected from the housing.

In an aspect, the alert is a sound.

In an aspect, the bottom cap has a trough for application for a topical anesthetic and/or analgesic.

In an aspect, the topical anesthetic is EMLA.

In an aspect, the bottom cap has a hole for ejection of the at least one microneedle.

In accordance with another aspect, there is provided a transdermal drug delivery device comprising:

a reservoir for holding a drug;

microneedles in fluid communication with the reservoir through which the drug can be delivered transdermally, a plunger for expelling the drug from the reservoir through the microneedles, and an outer covering enclosing the reservoir and the plunger and leaving the microneedles exposed.

In an aspect, the outer covering comprises ornamentation.

In an aspect, the ornamentation is selected so as to appeal to a child.

In an aspect, the reservoir is rigid.

In an aspect, the device further comprises a flange surrounding the periphery of the reservoir to which the outer covering is attached.

In an aspect, the flange comprises an adhesive for securing the drug delivery device such that the microneedles are facing the skin.

In an aspect, the device contains a predetermined dose of the drug in the reservoir.

In an aspect, the reservoir holds more than one drug.

In an aspect, the device comprises more than one reservoir.

In an aspect, each reservoir comprises a different drug.

In an aspect, there are two reservoirs.

In an aspect, the device comprises a separate plunger for each reservoir.

In an aspect, the device comprises a single plunger for simultaneously delivering the drug from each reservoir through the microneedles.

In an aspect, the plunger comprises a gasket.

In an aspect, the device further comprises a topical anesthetic and/or analgesic on the microneedles, the at least one microneedle or the plurality of microneedles.

In an aspect, the topical anesthetic and/or analgesic substantially seals the microneedles, the at least one microneedle or the plurality of microneedles to mitigate leakage of the drug before use.

In an aspect, the topical anesthetic is EMLA.

In accordance with another aspect, there is provided a transdermal drug delivery device comprising:

a reservoir for holding a drug, the reservoir comprising a height and a width; and microneedles in fluid communication with the reservoir through which the drug can be delivered transdermally, wherein the width is greater than the height.

In an aspect, the width is at least twice the height.

In an aspect, the width is at least three times the height.

In an aspect, the reservoir is rigid.

In an aspect, depression of the reservoir delivers the drug through the microneedles.

In an aspect, the device further comprises a plunger for delivering the drug from the reservoir through the microneedles.

In an aspect, the plunger comprises a gasket.

In an aspect, the device further comprises a flange surrounding the periphery of the reservoir.

In an aspect, the flange comprises an adhesive for securing the drug delivery device such that the microneedles are facing the skin.

In an aspect, the device further comprises an outer covering enclosing the reservoir and leaving the microneedles exposed.

In an aspect, the outer covering comprises ornamentation.

In an aspect, the ornamentation is selected so as to appeal to a child.

In an aspect, the device contains a predetermined dose of the drug in the reservoir.

In an aspect, the reservoir holds more than one drug.

In an aspect, the device further comprises more than one reservoir.

In an aspect, each reservoir comprises a different drug.

In an aspect, there are two reservoirs.

In an aspect, the device comprises a separate plunger for each reservoir.

In an aspect, the device comprises a single plunger for simultaneously delivering the drug from each reservoir through the microneedles.

In an aspect, the device is disguised as a bandage.

In an aspect, the device further comprises a topical anesthetic and/or analgesic on the microneedles.

In an aspect, the topical anesthetic and/or analgesic substantially seals the microneedles to mitigate leakage of the drug before use.

In an aspect, the topical anesthetic is EMLA.

In accordance with another aspect, there is provided a transdermal drug delivery device comprising:

a reservoir for holding a drug;

microneedles in fluid communication with the reservoir through which the drug can be delivered transdermally; and a topical anesthetic and/or analgesic coated on the exterior of the microneedles.

In an aspect, the topical anesthetic and/or analgesic substantially seals the microneedles to mitigate leakage of the drug before use.

In an aspect, the topical anesthetic is EMLA.

In an aspect, the reservoir is rigid.

In an aspect, depression of the reservoir delivers the drug through the microneedles.

In an aspect, the device further comprises a plunger for delivering the drug from the reservoir through the microneedles.

In an aspect, the plunger comprises a gasket.

In an aspect, the device further comprises a flange surrounding the periphery of the reservoir.

In an aspect, the flange comprises an adhesive for securing the drug delivery device such that the microneedles are facing the skin.

In an aspect, the device further comprises an outer covering enclosing the reservoir and leaving the microneedles exposed.

In an aspect, the device contains a predetermined dose of the drug in the reservoir.

In an aspect, the reservoir holds more than one drug.

In an aspect, the device comprises more than one reservoir.

In an aspect, each reservoir comprises a different drug.

In an aspect, there are two reservoirs.

In an aspect, the device comprises a separate plunger for each reservoir.

In an aspect, the device comprises a single plunger for simultaneously delivering the drug from each reservoir through the microneedles.

In accordance with another aspect, there is provided a transdermal delivery device comprising:

a housing comprising a reservoir for holding a drug, at least one microneedle in fluid communication with the reservoir, an actuator for deploying the at least one microneedle, and a plunger for delivering the drug transdermally, wherein the transdermal delivery device is concealed from view during operation thereof.

In an aspect, the actuator is a button.

In an aspect, the device further comprises fastening elements attachable to the housing and configured for securing the transdermal delivery device to a wearer.

In an aspect, the fastening elements conceal the housing from the wearer.

In an aspect, the fastening elements comprises ornamentation.

In an aspect, the ornamentation is selected so as to appeal to a child.

In an aspect, the device further comprises connecting tubing in fluid communication with the reservoir and the at least one microneedle.

In an aspect, the connecting tubing is flexible to allow for small movements between a first position before actuation of the at least one microneedle and a second position after actuation of the at least one microneedle.

In an aspect, the connecting tubing forms a substantially perpendicular connection with the reservoir and terminates in a substantially perpendicular intersecting portion of connecting tubing which engages with the at least one microneedle.

In an aspect, the device further comprises a finger rest area on a top casing of the housing.

In an aspect, the device contains a predetermined dose of the drug in the reservoir.

In an aspect, the reservoir holds more than one drug.

In an aspect, the device comprises more than one reservoir.

In an aspect, each reservoir comprises a different drug.

In an aspect, there are two reservoirs.

In an aspect, the device comprises a separate plunger for each reservoir.

In an aspect, the device comprises a single plunger for simultaneously delivering the drug from each reservoir.

In an aspect, the device further comprises an injection unit within the housing, wherein the injection unit comprises a bottom cap.

In an aspect, the bottom cap comprises a first indentation or void with a first position and a second indentation or void with a second position relative to the first position and wherein the first indentation or void lockingly engages one of a pair of protuberances on the actuator before actuation of the at least one microneedle and the second indentation or void lockingly engages with one of the pair of protuberances on the actuator after actuation of the at least one microneedle.

In an aspect, movement of the pair of protuberances before and after actuation alerts the user that the at least one microneedle has been ejected from the housing.

In an aspect, the alert is a sound.

In an aspect, the bottom cap has a trough for application for a topical anesthetic and/or analgesic.

In an aspect, the topical anesthetic is EMLA.

In an aspect, the bottom cap has a hole for ejection of the at least one microneedle.

In accordance with another aspect, there is provided a transdermal delivery device comprising:

a housing comprising a reservoir for holding a drug, an actuator unit comprising at least one microneedle in fluid communication with the reservoir, an injection unit comprising an actuator for deploying the at least one microneedle, and a plunger for delivering the drug transdermally, wherein the transdermal delivery device is disguised as a bandage.

In an aspect, the actuator is a button.

In an aspect, the device further comprises fastening elements attachable to the housing and configured for securing the transdermal delivery device to a wearer.

In an aspect, the fastening elements conceal the housing from the wearer.

In an aspect, the fastening elements comprises ornamentation.

In an aspect, the ornamentation is selected so as to appeal to a child.

In an aspect, the device further comprises connecting tubing in fluid communication with the reservoir and the at least one microneedle.

In an aspect, the connecting tubing is flexible to allow for small movements between a first position before actuation of the at least one microneedle and a second position after actuation of the at least one microneedle.

In an aspect, the connecting tubing forms a substantially perpendicular connection with the reservoir and terminates in a substantially perpendicular intersecting portion of connecting tubing which engages with the at least one microneedle.

In an aspect, the device further comprises a finger rest area on a top casing of the housing.

In an aspect, the device contains a predetermined dose of the drug in the reservoir.

In an aspect, the reservoir holds more than one drug.

In an aspect, the device comprises more than one reservoir.

In an aspect, each reservoir comprises a different drug.

In an aspect, there are two reservoirs.

In an aspect, the device comprises a separate plunger for each reservoir.

In an aspect, the device comprises a single plunger for simultaneously delivering the drug from each reservoir.

In an aspect, the injection unit further comprises a bottom cap.

In an aspect, the bottom cap comprises a first indentation or void with a first position and a second indentation or void with a second position relative to the first position and wherein the first indentation or void lockingly engages one of a pair of knobs on the actuator before actuation of the at least one microneedle and the second indentation or void lockingly engages with one of the pair of protuberances on the actuator after actuation of the at least one microneedle.

In an aspect, movement of the pair of protuberances before and after actuation alerts the user that the at least one microneedle has been ejected from the housing.

In an aspect, the alert is a sound.

In an aspect, the bottom cap has a trough for application for a topical anesthetic and/or analgesic.

In an aspect, the topical anesthetic is EMLA.

In an aspect, the bottom cap has a hole for ejection of the at least one microneedle.

In an aspect, the reservoir is removable from the housing thereby defining a space in the housing.

In an aspect, a barrel snuggly fits in the spaced defined by the reservoir.

In an aspect, the barrel is capable of holding a drug.

In an aspect, the barrel is connectable to a portable base unit device for delivery of the drug and/or deployment of the at least one microneedle.

In an aspect, the barrel has the shape of a syringe.

In an aspect, the drug is titratable.

In accordance with another aspect, there is provided a cuff comprising the transdermal drug delivery device described herein.

In accordance with another aspect, there is provided a use of the transdermal drug delivery device described herein or the cuff described herein for delivering a drug transdermally to a subject.

In an aspect, the use is for sedating a subject.

In an aspect, the use is for vaccinating a subject.

In an aspect, the use is for reversing the effect of a sedative in a subject

In an aspect, the subject is a child.

In accordance with another aspect, there is provided a method of delivering a drug transdermally, the method comprising depressing the reservoir of the drug delivery device described herein so that the drug is expelled through the microneedles and into the skin of a subject.

In accordance with another aspect, there is provided a method of delivering a drug transdermally, the method comprising depressing the reservoir of the drug delivery device described herein so that the drug is expelled through the at least one microneedle and into the skin of a subject.

In accordance with another aspect, there is provided a method of delivering a drug transdermally, the method comprising depressing the reservoir of the drug delivery device described herein so that the drug is expelled through the plurality of microneedles and into the skin of a subject.

In an aspect, the method is for sedating a subject.

In an aspect, the method is for vaccinating a subject.

In an aspect, the method is for reversing the effect of a sedative in a subject.

In an aspect, the subject is a child.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from said detailed description.

DESCRIPTION OF THE FIGURES

The present invention will be further understood from the following description with reference to the Figures, in which.

DETAILED DESCRIPTION

Figure 1:
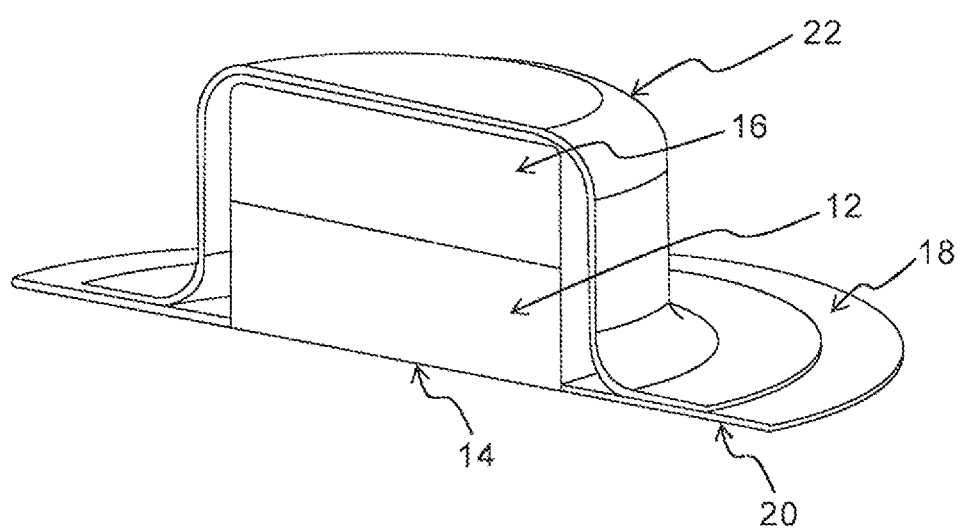
FIG. 1 shows a perspective cross-sectional view of a drug delivery device described herein.

Management of behaviour and anxiety in subjects, particularly children, during medical or dental procedures often requires administration of pharmacologic agents. The choice for routes of administration of such agents is limited as they themselves are anxiety producing and compliance is unreliable. Indeed, administration of sedative and/or anxiolytic drugs to young children that are relatively painless, easy to administer, and that do not produce anxiety-related behaviour problems in young children is a problem at present, given currently available options, including administration of drugs orally, intranasally, parenterally by injection, or by inhalation of drugs in a gaseous form.

All of the above modalities suffer from one or more of the following problems: 1. Unreliability of the drug available for its therapeutic effect; 2. The first pass effect, which renders a portion of the drug useless for the intended purpose; 3. The painfulness of the injection or spray; 4. The anxiety associated with the mode of administration; 5. The requirement for specialized equipment; 6. The cost of administration; 7. The risks and side effects. The drug delivery device described herein, in aspects, reduces or eliminates many of these problems.

A relatively painless, effective, and efficient route of administration is described herein for accomplishing moderate levels of sedation in subjects, such as children, that will permit the safe and thorough completion of the required medical or surgical intervention to be carried out.

Provided herein is, in aspects, a transdermal microneedle patch, drug delivery system for short duration procedural sedation with one or more sedative-anxiolytic drugs and/or the reversal of said sedation, for use in pediatrics or pediatric dentistry. In aspects, the drug delivery device includes age and/or weight-appropriate sedative-anxiolytic drug combinations in pre-dosed, optionally skin adherent, patch-like reservoir(s) with a microneedle or microneedle array that is capable of delivering the drugs transdermally in a painless or near-painless manner in young children below the age of about 6 years.

The drug delivery devices described herein typically include one and, optionally, a plurality of, microneedle(s) and at least one reservoir that is in fluid connection with one or more of the microneedles. Typically, the microneedles are secured to or are an integral part of the reservoir. In aspects, the microneedles are provided as a multi-dimensional array which may or may not be arranged in geometric patterns. In aspects, the microneedles are provided a single microneedle or single row of microneedles. The microneedle device can be adapted to be a single-use, disposable device, or can be adapted to be fully or partially reusable. In aspects, the device is automated and/or remotely operable, so that it can be used without directly touching the patient after applying the device.

In a typical aspect, the microneedle tips are coated and/or plugged with an anaesthetic, typically a thermally activated, topical skin anaesthetic gel which serves two purposes: 1. to provide topical anaesthesia to overcome even minor discomfort that might be experienced by the penetration of the microneedle(s) into the skin or the pain caused by tissue distension when the drug is deposited into the epidermal tissue; and 2. to serve as a plug or seal at the ends of the microneedle tips, thereby holding the drug in the reservoir until it is deposited into the tissues with the application of pressure.

Figure 3:
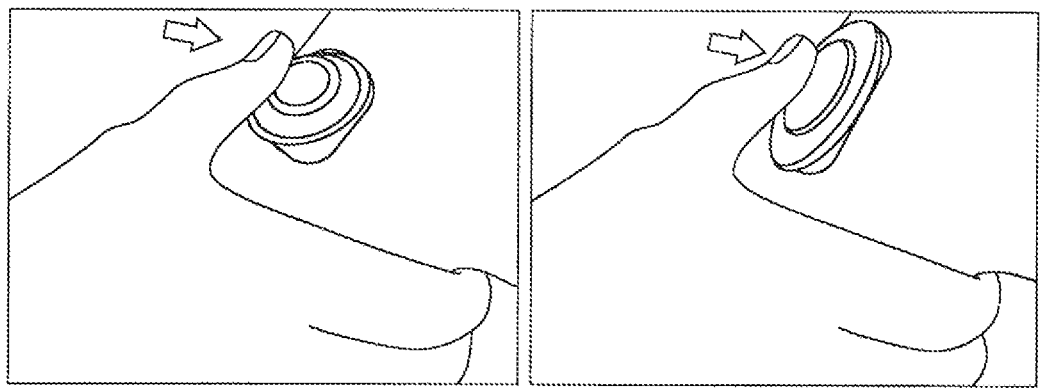
FIG. 3 shows a perspective view of the drug delivery device of FIG. 1 in use, in both resting and compressed configurations.

Typically, drug administration is activated mechanically by applying pressure with a thumb or finger (FIG. 3). In aspects, the drug is administered in an automatic fashion (e.g., without requiring applying the pressure of the thumb or finger). This provides a relatively painless delivery system that is suitable for use in young children for short duration procedural sedation and/or for accomplishing moderate levels of sedation. Advantageously, in aspects, the drug delivery device described herein permits safe and thorough completion of the required medical or surgical intervention.

In typical use, the transdermal microneedle patch with a thermally activated topical anesthetic gel is applied to the skin on the upper arm of a child using an adhesive backing. In other aspects, the transdermal microneedle patch is applied to the skin on the upper arm of a child using fastening elements, such as a band or a cuff, which may resemble a blood pressure cuff, that can fit comfortably around the arm of the child. In aspects, the fastening elements are decoratively covered to distract the child receiving the needle. The typical location for application will be over the deltoid muscle of the child. The patch will be left in place for approximately 10 minutes allowing the thermally activated topical anesthetic gel to provide surface anesthesia. Following the 10 minute application of the patch, the drug will be injected into the dermis, via an automatic method (described below) or a manual method with the application of thumb pressure while stabilizing and providing opposing pressure with the fingers of the same hand (FIG. 3). It will be understood that the device could be applied to other bodily locations, such as the upper thigh, the lower arm or lower leg, or the abdomen, for example.

Definitions

The term "subject" as used herein refers to any member of the animal kingdom, typically a mammal. The term "mammal" refers to any animal classified as a mammal, including humans, other higher primates, domestic and farm animals, and zoo, sports, or pet animals, such as dogs, cats, cattle, horses, sheep, pigs, goats, rabbits, etc. Typically, the mammal is human and even more typically, the mammal is a human child under the age of 16, 15, 14, 13, 12, 11, 10, 9, 8, 7, 6, 5, 4, 3, or 2.

Administration "in combination with" one or more further pharmacologic agents includes simultaneous (concurrent) and consecutive administration in any order.

The term "pharmaceutically acceptable" means that the compound or combination of compounds is compatible with the remaining ingredients of a formulation for pharmaceutical use, and that it is generally safe for administering to humans according to established governmental standards, including those promulgated by the United States Food and Drug Administration.

The term "pharmaceutically acceptable carrier" includes, but is not limited to solvents, dispersion media, coatings, antibacterial agents, antifungal agents, isotonic and/or absorption delaying agents and the like. The use of pharmaceutically acceptable carriers is well known.

The term "biological barrier" is intended to encompass any such barrier, such as the skin, mucous membranes, the eye, and blood vessel walls, for example. Typically, the biological barrier is the skin.

In understanding the scope of the present application, the articles "a", "an", "the", and "said" are intended to mean that there are one or more of the elements. Additionally, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

It will be understood that any aspects described as "comprising" certain components may also "consist of" or "consist essentially of," wherein "consisting of" has a closed-ended or restrictive meaning and "consisting essentially of" means including the components specified but excluding other components except for materials present as impurities, unavoidable materials present as a result of processes used to provide the components, and components added for a purpose other than achieving the technical effect of the invention. For example, a composition defined using the phrase "consisting essentially of" encompasses any known pharmaceutically acceptable additive, excipient, diluent, carrier, and the like. Typically, a composition consisting essentially of a set of components will comprise less than 5% by weight, typically less than 3% by weight, more typically less than 1% by weight of non-specified components.

It will be understood that any component defined herein as being included may be explicitly excluded from the claimed invention by way of proviso or negative limitation. In addition, all ranges given herein include the end of the ranges and also any intermediate range points, whether explicitly stated or not.

Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

Figure 2:
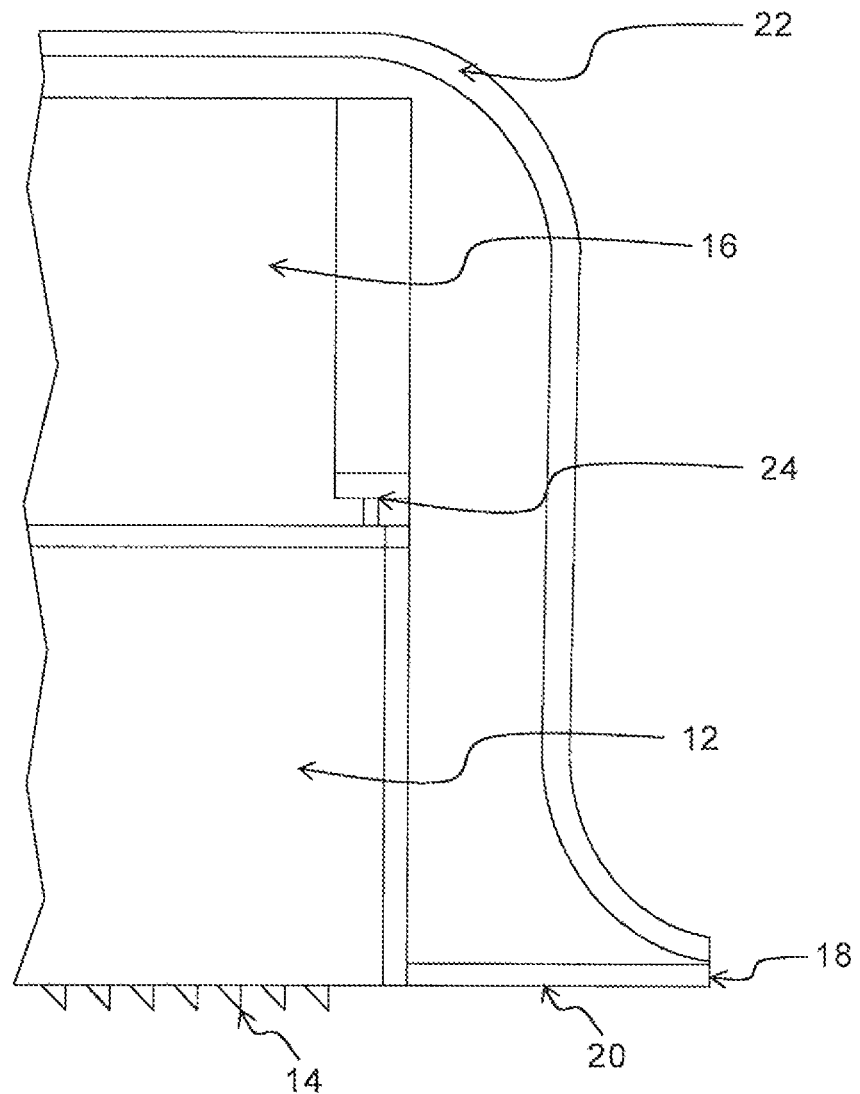
FIG. 2 shows an elevation cross-sectional view of the drug delivery device of FIG. 1.

Turning now to FIGS. 1 and 2, a drug delivery device 10 is shown. The drug delivery device comprises a reservoir 12 for containing the pharmacological agent to be delivered. Integral with the reservoir 12 is a plurality of microneedles 14 in a substantially homogeneous array. A plunger 16 is positioned on top of the reservoir 12 so that the plunger 16 can be depressed to cause deformation of the reservoir 12 and thereby force the pharmacological agent out of the reservoir 12, through the microneedles 14, and into the skin.

The drug delivery device 10 comprises a peripheral flange 18, upon which an adhesive 20 can be applied for securing the drug delivery device 10 to the skin. The entire drug delivery device is covered with an outer covering 22, which can contain different designs, colours, characters, or other ornamentation to help put the subject at ease.

As most clearly shown in FIG. 2, a rubber gasket 24 is disposed between the plunger 16, the reservoir 12, and the outer covering 22 to facilitate movement within the outer covering 22 and deformation of the reservoir 12 upon depression of the plunger 16.

The drug delivery device 10 is shown in use in FIG. 3. In a typical aspect, a topical anesthetic and/or analgesic is applied to the microneedles 14 on their exterior surface or to the skin of the subject where the drug delivery device 10 is to be adhered. The drug delivery device 10 is then adhered to the skin. Care can be taken at this point to avoid applying pressure to the drug delivery device for a set period of time, sufficient for the topical anesthetic and/or analgesic to take effect, for example, for about 10 minutes. After that period of time, the plunger 16 is depressed, thereby deforming the reservoir 12 and forcing the pharmacological agent out through the microneedles 14 into the skin, typically painlessly and without undue anxiety on the part of the subject.

Figure 4:
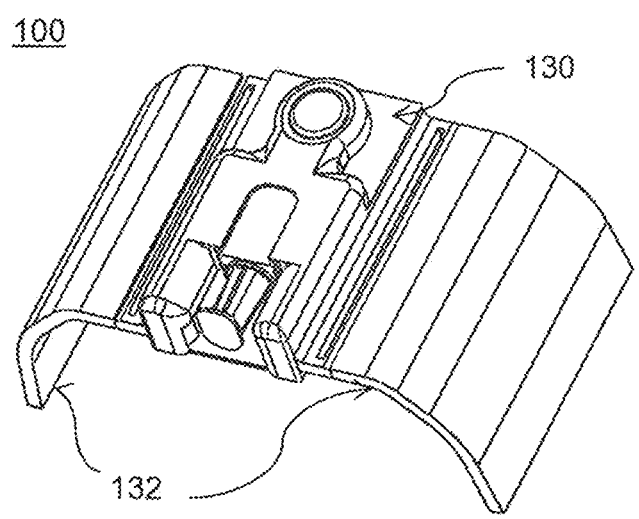
FIG. 4 shows a perspective view of an embodiment of a drug delivery device, in an open configuration, described herein.

In another embodiment, the drug delivery device 100 described herein is provided (FIG. 4). The drug delivery device 100 comprises a housing 130 and fastening elements 132 for releasably securing the drug delivery device 100 to the child. Typically, the fastening elements 132 conceal the housing 130 so that the child is distracted from the injection of a needle (not shown) while the device 100 is about the child's arm.

Figure 5:
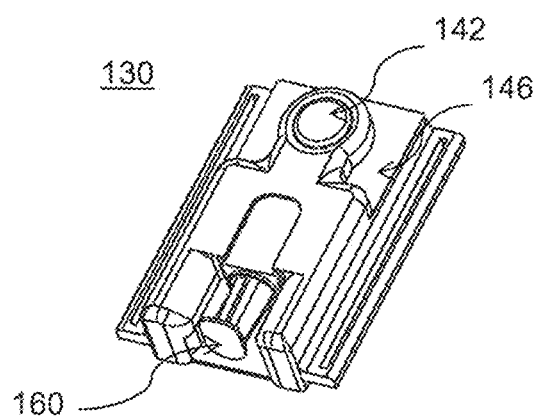
FIG. 5 shows a perspective view of the embodiment of FIG. 4 without fastening elements described herein.
Figure 6:
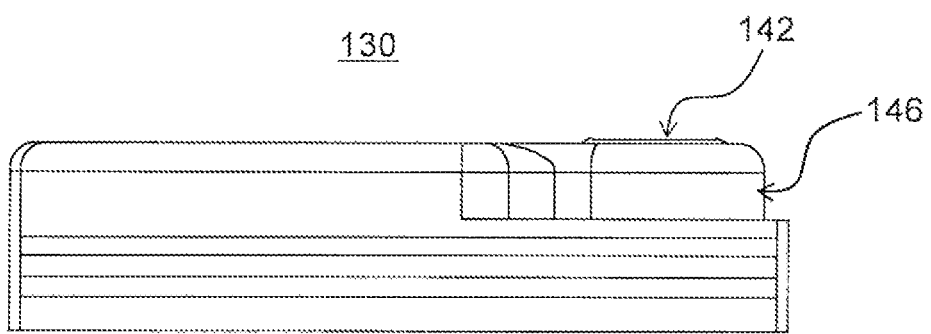
FIG. 6 shows a side view of the embodiment FIG. 5.

As shown in FIG. 5, the housing 130 comprises an actuator 142 for needle delivery and a plunger 160 for delivering the drug from a reservoir 120 to the microneedle bore as described herein. The housing 130 further comprises a top casing 146. Typically, the reservoir 120 is housed under the top casing 146. The actuator 142, such as, a deployable button, can be pressed to actuate a needle (not shown) for penetration into the skin. The plunger 160 can be pushed to deliver the drug into the skin by depression of the reservoir 120. Typically, the actuator 142 is enclosed in a raised bore on the surface of the housing 130. In aspects, the actuator 142 may protrude above the top casing 146, as shown in FIG. 6. However, it is contemplated that the actuator 142 may also be depressed into the raised bore (not shown). One skilled in the art would understand that the level of depression into the raised bore could only be as deep as that which still allows the actuator 142 to be operated (e.g., pressed) by the user.

Figure 7:
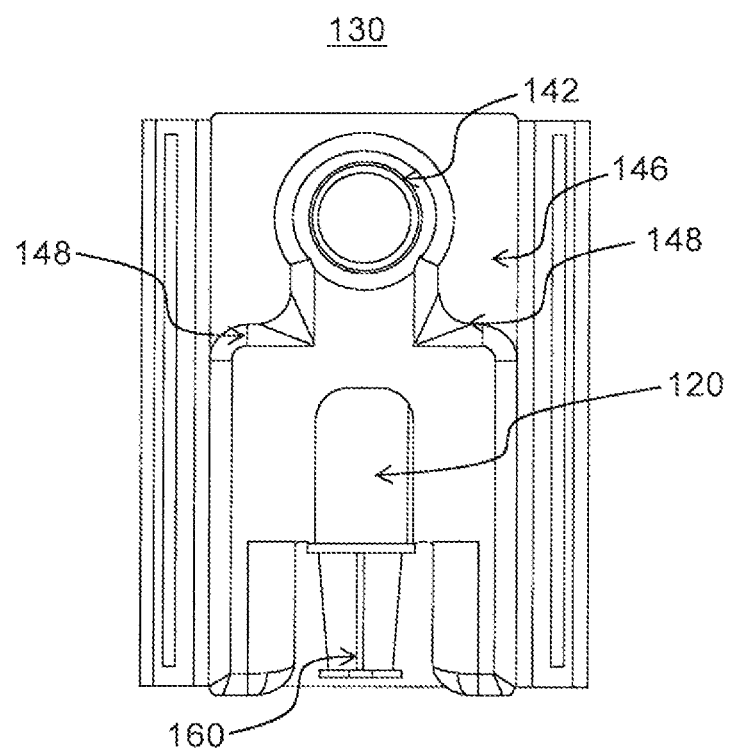
FIG. 7 shows a top view of the embodiment of FIG. 5.

As shown in FIG. 7, the housing 130 further comprises at least one finger rest area 148 on the top casing 146. Typically, there are at least two finger rest areas 148 laterally spaced apart on the top casing 146 of the housing 130. One skilled in the art would appreciate that the orientation of the at least two finger rest areas 148 can be varied, such that, for example, they may be proximal to either the lateral edge of the housing 130 or the longitudinal edge of the housing 130. The position of the finger rests areas 148 depends on the requirements of the device 100.

Figure 8:
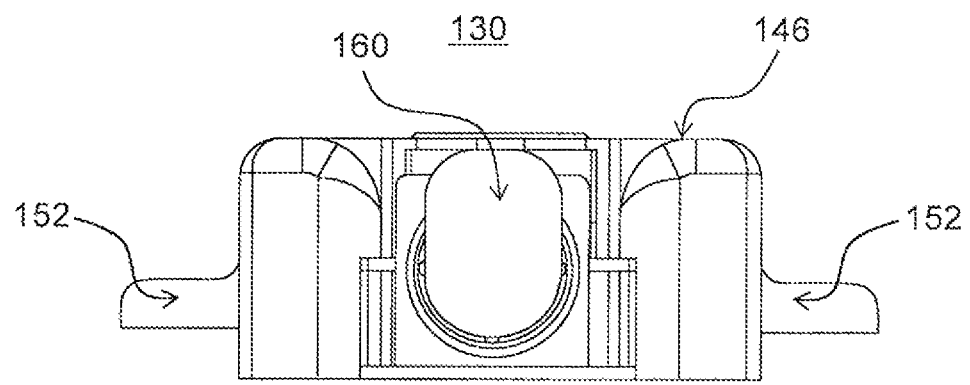
FIG. 8 shows a side view (from the plunger) of the embodiment of FIG. 5.

As shown in FIG. 8, the housing 130 may comprise at least two connectors 152 for attaching the fastening elements 132 to the housing 130. Typically, the connectors 152 extend laterally from at least a portion of a side of the housing 130.

Figure 9:
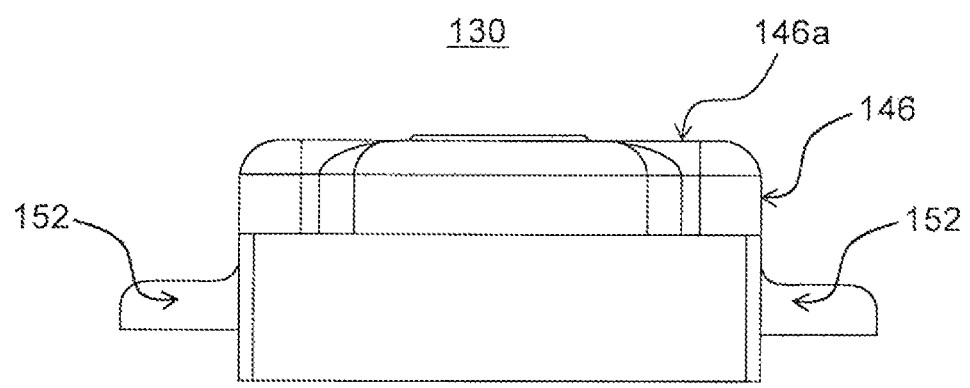
FIG. 9 shows a side view (from the actuator) of the embodiment FIG. 5.

In aspects, the relative position of the connectors 152 may be varied. As shown in FIG. 9, the connectors 152 are positionable at a top surface 146a of the top casing 146. In this way, when the fastening elements 132 are attached to the connectors 152, the housing 130 is fully concealed from the patient when the device 100 is worn. However, one skilled in the art would appreciate that the connectors 152 may be found at any connectable position along the later surface of the housing 130.

Figure 10:
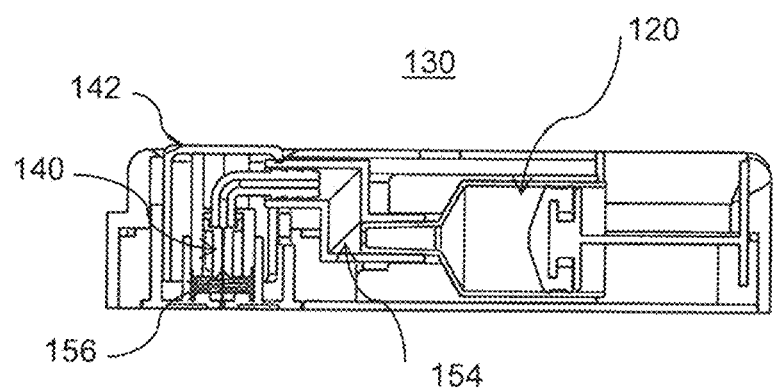
FIG. 10 shows a cross-sectional view of the housing of the device, described herein.

As shown in FIG. 10, an assembly of the plunger 160, the reservoir 120 and a needle 140 (in a non-actuated stated) is shown. The cross-sectional view shows how the reservoir 120 mates with the interior walls of the device 100 so that the reservoir 120 may be removable. The reservoir 120 and the needle 140 are connected via a connecting tubing 154. Typically, the connecting tubing 154 is flexible to allow for small movement between the original and actuated positions of the needle 140. The connecting tubing 154 allows for movement of a drug from the reservoir 120 to the needle 140 for injection into the skin. The connecting tubing 154 can take on any path construction necessary to allow for delivery of the drug from the reservoir 120 to the needle 140. Typically, the connecting tubing 154 a path that is substantially perpendicular to a tip of the reservoir 120 and terminating in a substantially perpendicular intersecting portion of tubing leading to engagement with the needle 140. One skilled in the art would understand that the construction of the path of the connecting tubing 154 will depend on the requirements of the device 100. A spring 156 found within the housing 130 is responsible for keeping the actuator 142 and the needle 140 in place before actuation.

Figure 11:
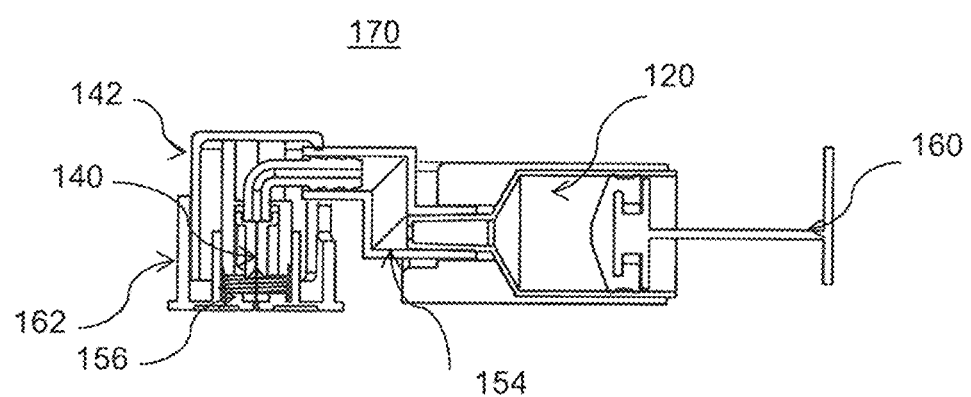
FIG. 11 shows a cross-sectional view of an injection unit of the housing of FIG. 10.
Figure 12:
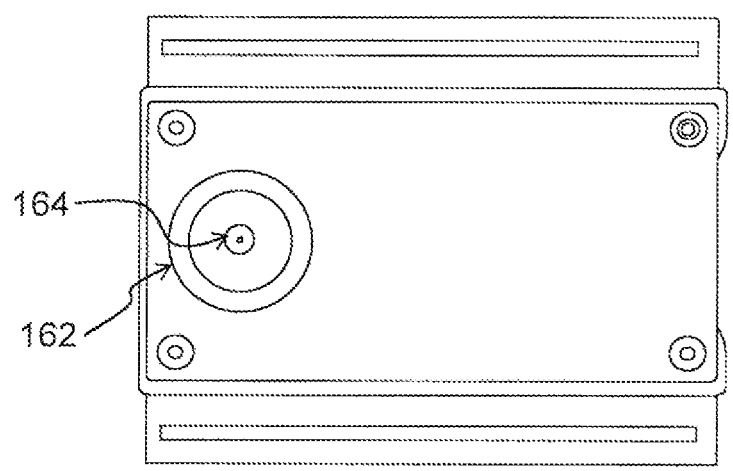
FIG. 12 shows a bottom view of the housing of the device without fastening elements described herein.
Figure 13:
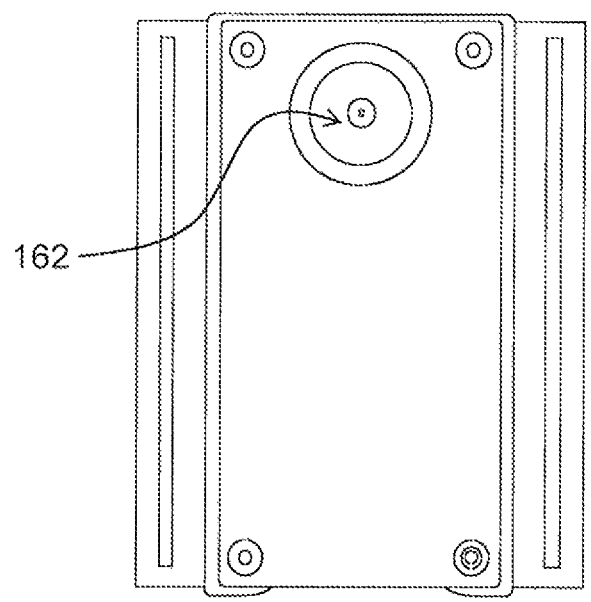
FIG. 13 shows a bottom view of the housing of the device without fastening elements described herein.
Figure 14:
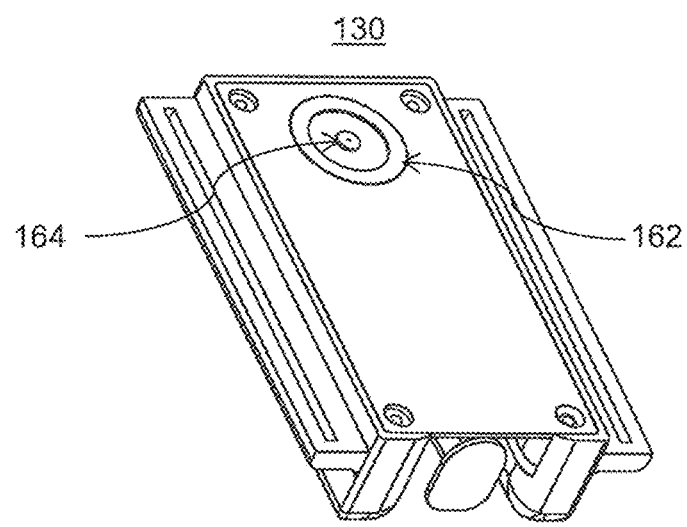
FIG. 14 shows a perspective view of the bottom of the housing of the device, without fastening elements, described herein.
Figure 15:
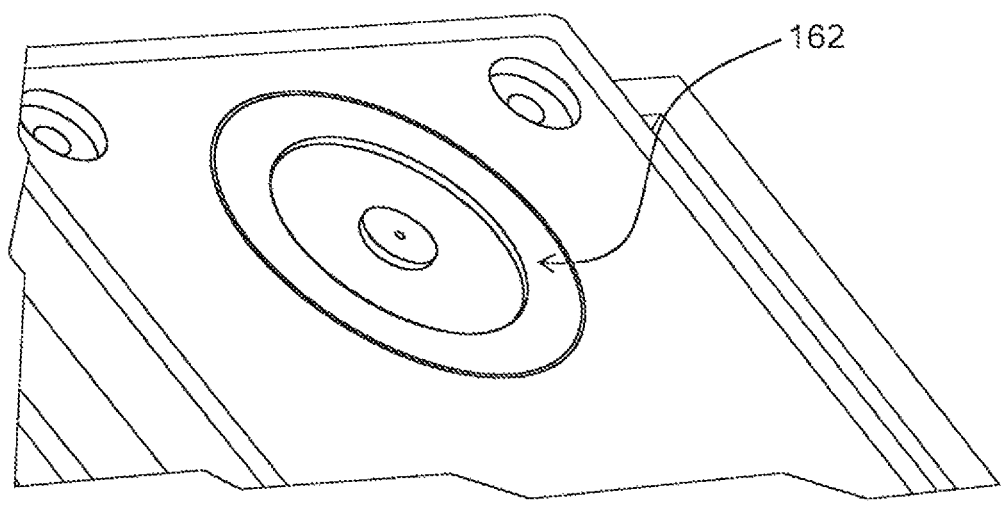
FIG. 15 shows a close-up view of an injection hole of the bottom of the housing of FIG. 14 before actuation, described herein.

An embodiment of the device 100 showing an injection unit 170 is shown in FIG. 11. The injection unit 170 comprises the actuator 142 and a bottom cap 162. The bottom cap 162 houses the needle 140 and the spring 156.

As shown in FIGS. 12-15, the bottom cap 162 has a hole 164 at the centre thereof, to allow the needle 140 to exit the housing 130 upon actuation. Typically, the hole 164 is sized to provide frictionless motion of the needle 140 through the hole 164. Typically, the bottom cap 162 has a circular trough for depositing anesthetic and/or analgesic gel on the bottom surface thereof (see, FIGS. 14 and 15). One skilled in the art would appreciate that the trough does not need be circular, but can take on any shape, so long as it provides a surface upon which the gel may be applied. The trough thus provides a surface for which the anesthetic and/or analgesic gel, when applied thereto, can numb the surface of the biological barrier (e.g., skin) when deposited thereon. In this way, the anesthetic gel reduces the pain caused by the penetration of the needle 140.

Alternatively, the gel may be applied to the skin directly, whereby the trough provides a space between the hole 164 and the skin so that an appropriate depth of penetration may be obtained from the needle 140. When not in use, the hole 164 may be covered with a protective covering to prevent accidental needle pricks.

An actuation unit 190 of the device 100 is shown before (FIG. 16) and after (FIG. 17) actuation of the needle 140, respectively. The bottom cap 162 has a first indentation or void, such as a slit 204a and a second indentation or void, such as a slit 204b. These slits 204a and 204b and the protuberances 202 (described below) provide the device 100 and/or the housing 130 with built-in stops and/or a locking mechanism allowing for a pre-determined precise depth of needle penetration into the skin of the patient (described below).

Figure 16:
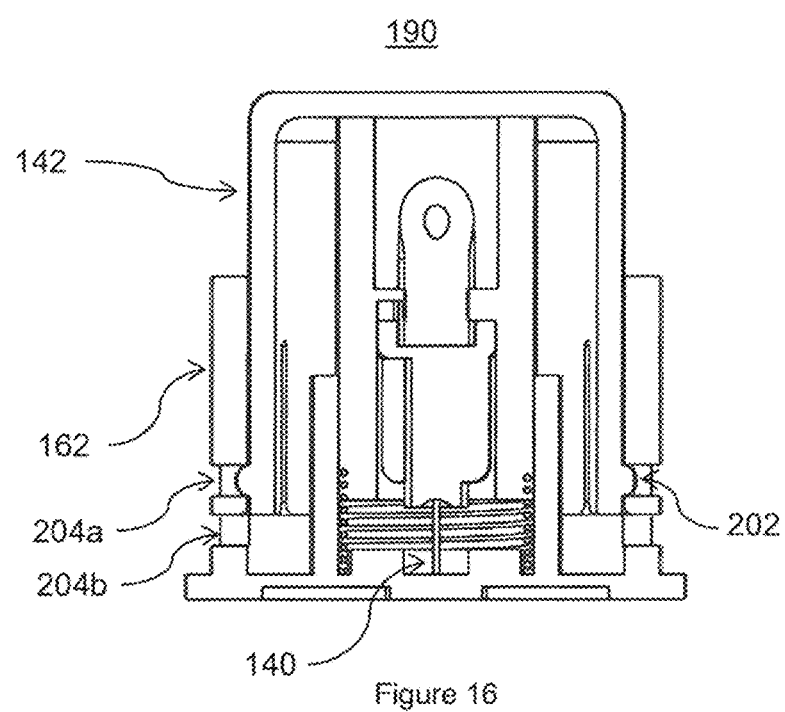
FIG. 16 shows a cross-sectional view of an actuation unit of the device, before actuation, described herein.
Figure 17:
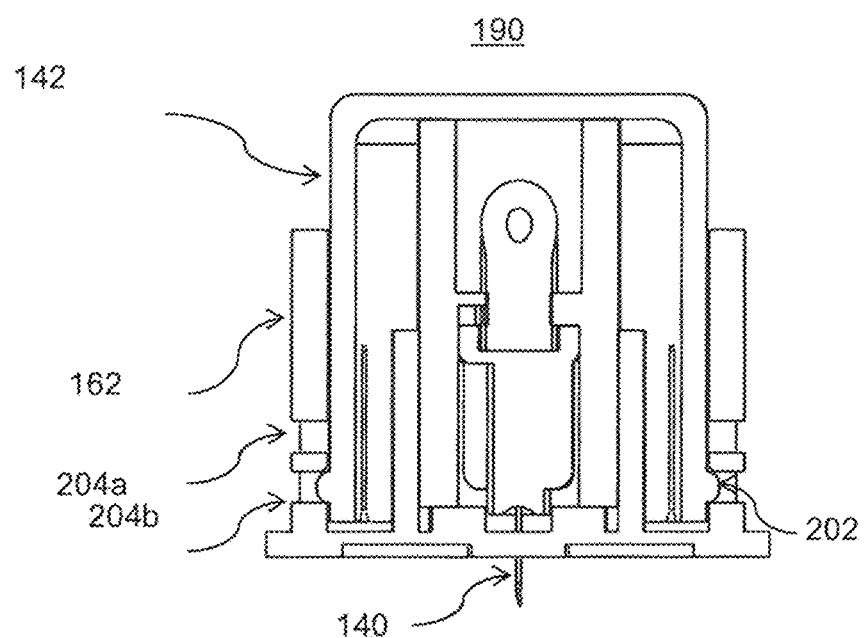
FIG. 17 shows a cross-sectional view of the actuation unit of FIG. 16, after actuation, described herein.

Typically, the first and second slits 204a, 204b provide a locking feature for a pair of outwardly extending protuberances 202, found on a surface of the substantially parallel opposing walls of the actuator 142. As shown in FIG. 16, at the original position, the protuberances 202, are locked at the first slit 204a. When the needle 140 is actuated, the actuator 142 causes the protuberances 202 to move to the second slit 204b. The movement, such a jumping action of the protuberance 202 between the first and second slits 204a and 204b, causes the protuberances 202 to hit an inner wall of the bottom cap 162. This produces a knocking sound which can alert the user that the needle 140 has been inserted into the skin.

Typically, the needle 140, upon actuation, will be pushed out of the device 100 and penetrate the biological barrier (e.g., the skin) from about 1 mm to 8 mm deep. The penetration may be about 1 mm deep, about 2 mm deep, about 3 mm deep, about 4 mm deep, about 5 mm deep, about 6 mm deep, about 7 mm deep or about 8 mm deep. In aspects, the penetration is about 1 to about 2 mm deep. In aspects, the penetration is about 4 to about 8 mm deep.

Figure 18:
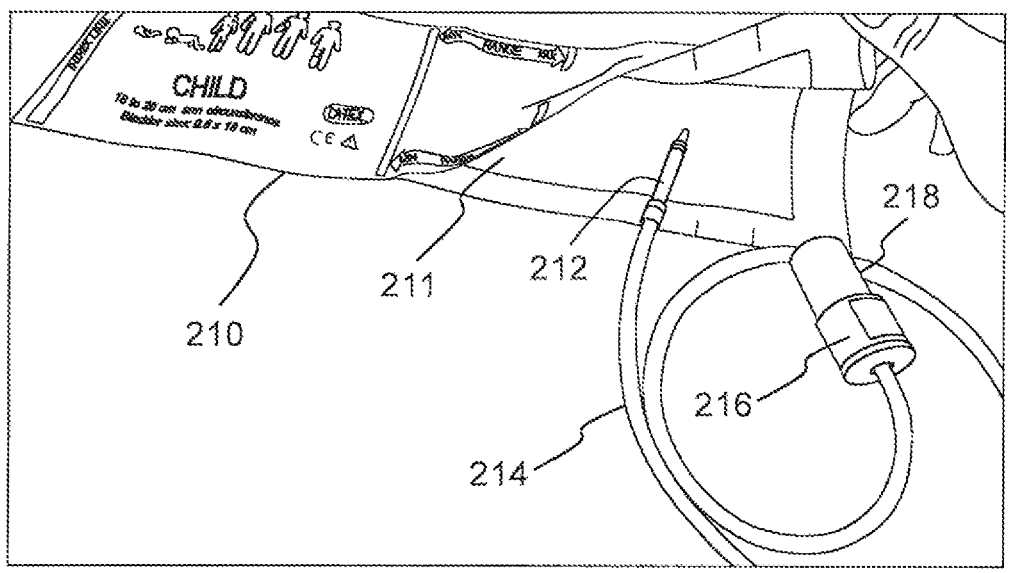
FIG. 18 shows a perspective view of a cuff in an open configuration ready for concealment of the drug delivery device described herein.
Figure 19:
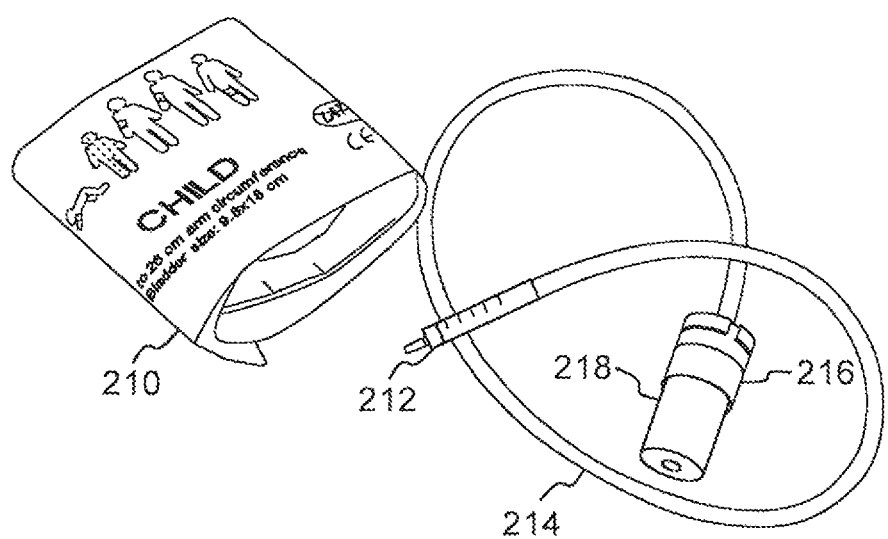
FIG. 19 shows a perspective view of the cuff of FIG. 18 in a closed configuration.

As shown in FIGS. 18 and 19, a cuff 210 is shown with the associated tubing 214 for delivery of the drug by the device 100 described herein. The device 100 as described herein can also be concealed within the cuff 210 in order to distract the patient of the impending micro-injection procedure.

The cuff 210 comprises a covering or sleeve 211 for concealing the device 100 described herein. The cuff 210 is connected to a portable base unit (not shown) via a tubing 214. The tubing 214 has a first end terminating in a barrel 212 and the second end terminating in a tube connector 216. The barrel 212 is shown in a removed state, but one skilled in the art would appreciate that since the reservoir 120 described herein is removable from the housing 130, an outer wall of the barrel 212 is readily available to mate with the interior walls of the housing 130. In this way, when the barrel 212 secured within the housing 130 of the device 100, drug may be delivered in an automated fashion to the microneedle 140 for transdermal delivery as described herein.

The tube connector 216 is attachable to a base unit connector 218 for connection of the tubing 214 to the portable base unit (not shown). Typically, by pressing a button on the portable base unit (not shown) the tubing 214 allows the automated passage of the drug from the barrel 212 to the microneedle 140 via a pump in the portable base unit (not shown). By pressing another button on the portable base unit (not shown) the microneedle 140 can be automatically injected into the skin of the patient. In aspects, the automatic injection of the microneedle 140 into the skin of the patient is coupled with locking the microneedle 140 into the injected position for the duration of the procedure.

In typical aspects, the barrel 212 terminates in a generally pointed tip and is engageable with the device 100 described herein. In aspects, the barrel 212 may be graduated on the surface thereof (see, FIGS. 18 and 19) as an indicator of the volume of drug for delivery therefrom. Typically, the barrel 212 snugly fits into the space previously occupied by the reservoir 120 of the device 100 (see, FIG. 10). The barrel 212 is in fluid connection with the microneedle 140 via connecting tubing 154. When assembled in this way, when the user presses a button on the portable base unit (not shown), automation of drug delivery from the barrel 212 to the microneedle 140 and/or ejection of the microneedle 140 is provided.

In aspects, the base connector 218 is connected to the portable base unit (not shown) such that tubing 214 can be attached to the barrel 212 and the barrel 212 inserted into the device 100 as described herein for delivery of the drug. In other aspects, the tubing 214 is attached to the cuff 210, with the device 100 concealed by the cuff 210, and thus, the base connector 218 needs only to be connected to the portable base unit (not shown) for operation of the device.

Microneedle(s)

The one or more microneedles are typically hollow shafts, so that the pharmacological agent or drug can flow from the reservoir, through the microneedles, and into the skin; that is, each microneedle contains at least one substantially annular bore or channel having a diameter large enough to permit passage of a drug-containing fluid and/or solid material through the microneedle. The hollow shafts may be linear, meaning that they extend upwardly from needle base to needle tip, or they may take a more complex path and, for example, extend upwardly from the needle base, but then lead to one or more 'portholes' or 'slits' on the sides of the needles, rather than an opening at the needle tip.

The one or more microneedles can be constructed from a variety of materials, including metals, ceramics, semiconductors, organics, polymers, and/or composites. Typical materials of construction include surgical grade stainless steel, gold, titanium, nickel, iron, tin, chromium, copper, palladium, platinum, alloys of these or other metals, silicon, silicon dioxide, ceramics and/or polymers. Representative biodegradable polymers include polymers of hydroxy acids such as lactic acid and glycolic acid polylactide, polyglycolide, polylactide-co-glycolide, and copolymers with PEG, polyanhydrides, poly(ortho)esters, polyurethanes, poly(butyric acid), poly(valeric acid), and poly(lactide-co-caprolactone). Representative non-biodegradable polymers include polycarbonate, polyester, and polyacrylamides.

The one or more microneedles typically have sufficient mechanical strength to remain intact while being inserted into the biological barrier, while remaining in place for from a few seconds up to a number of days, and while being removed. In embodiments where the microneedles are formed of biodegradable polymers, the microneedle remains intact at least long enough for the microneedle to serve its intended purpose (e.g., its conduit function for delivery of drug). Before initial use, the microneedles are typically sterilized using standard methods such as ethylene oxide, gamma irradiation, or autoclaving and are therefore typically fabricated from a material that is sterilisable.

The one or more microneedles can have straight or tapered shafts. In a typical aspect, the diameter of the microneedle is greatest at the base end of the microneedle and tapers to a point at the end distal the base. The microneedle can also be fabricated to have a shaft that includes both a straight (untapered) portion and a tapered portion. The needles may also not have a tapered end at all, for example, they may simply be cylinders with blunt or flat tips. A hollow microneedle that has a substantially uniform diameter, but which does not taper to a point, is referred to herein as a "microtube." As used herein, the term "microneedle" includes both microtubes and tapered needles unless otherwise indicated.

In aspects, the one or more microneedles have a single bevel suitable for penetrating into the skin of the patient. In other aspects, the one or more microneedles have multiple (e.g., two or more) bevels for penetrating into the skin of the patient. One skilled in the art would understand that the number of bevels provided by the microneedles can be varied dependent on the requirements of the device.

The one or more microneedles can be oriented perpendicular or at an angle to the reservoir. Typically, the microneedles are oriented perpendicular to the reservoir so that a larger density of microneedles per unit area of substrate can be provided. An array of microneedles can include a mixture of microneedle orientations, heights, or other parameters.

The one or more microneedles can be formed with shafts that have a circular cross-section in the perpendicular direction, or the cross-section can be non-circular. For example, the cross-section of the microneedle can be polygonal (e.g. star-shaped, square, triangular), oblong, or another shape. The shaft can have one or more bores. The cross-sectional dimensions typically are between about 1 μm and 500 μm, and typically between 10 and 100 μm. The outer diameter is typically between about 10 μm and about 100 μm, and the inner diameter is typically between about 3 μm and about 80 μm.

In one embodiment the cross-sectional dimensions are designed to leave a residual hole (following microneedle insertion and withdrawal) of less than about 0.2 μm, to avoid making a hole which would allow bacteria to enter the penetration wound. The actual microneedle diameter will typically be in the few micron range, since the holes typically contract following withdrawal of the microneedle. Larger diameter and longer microneedles are acceptable, so long as the microneedle can penetrate the biological barrier (typically skin) to the desired depth.

The length of the one or more microneedles typically is between about 10 μm and 1 mm, typically between 100 μm and 1000 μm, and more typically between 100 μm and 500 μm or between 150 μm and 350 μm. The length is selected for the particular application, accounting for both an inserted and uninserted portion. An array of microneedles can include a mixture of microneedles having, for example, various lengths, outer diameters, inner diameters, cross-sectional shapes, and spacings between the microneedles, however, typically, the array contains a substantially homogeneous set of microneedles, with consistent sizes, shapes, and spacings.

In transdermal applications, the "insertion depth" of the one or more microneedles is typically less than about 1000 μm, so that insertion of the microneedles into the skin does not penetrate into the dermis, thereby avoiding contacting nerves which may cause pain. In such applications, the actual length of the microneedles typically is longer, since the portion of the microneedles distal the tip may not be inserted into the skin; the uninserted length depends on the particular device design and configuration. The actual (overall) height or length of microneedles should be equal to the insertion depth plus the uninserted length.

In typical aspects, the one or more microneedles may be pre-coated and/or plugged with a topical anesthetic or analgesic or a topical anesthetic or analgesic may be separately applied before application of the microneedles to the skin. Suitable topical anesthetics and analgesics would be known to a skilled person and include, for example, EMLA, benzocaine, xylocaine, ketocaine, salicytates, such as methyl salicylate andtrolamine salicylate, lidocaine, prilocaine, tetracaine, pramoxine, dibucaine, ibuprofen, diclofenac, capsaicin, menthol, camphor, and combinations thereof. Typically, the topical anesthetic is EMLA, which is a 5% emulsion preparation, containing 2.5% each of lidocaine/prilocaine, marketed by APP Pharmaceuticals and indicated for dermal anesthesia.

In a particular aspect, the device described herein comprises a single microneedle. In other aspects, the device comprises 2 microneedles. The device may contain from 1 to about 100 microneedles, such as 1, 2, 3, 4, 5, 6, 7, 8, 9, 10, 20, 25, 30, 35, 50, 75, or 100 microneedles. In certain aspects where more than one drug is to be delivered, or more than one dose of the same drug is to be delivered, each drug or dose may be delivered from the same or a separate microneedle.

Reservoir

The reservoir is in fluid connection with the microneedle bore, such that the reservoir contents can flow from the reservoir and out through the microneedle tip, into the target tissue. Typically, it is attached to, or integrated with, the microneedle or microneedle array, either integrally (as in a one-piece device) or as a separately attached piece. In aspects, the reservoir is in fluid connection with the microneedle bore through connecting tubing. Typically, the reservoir provides suitable, leak-free storage of the drug composition before it is to be delivered. Typically, the reservoir also keeps the drug composition free of contaminants and degradation-enhancing agents. For example, the reservoir may exclude light when the drug composition contains photo-sensitive materials, and may include an oxygen barrier material in order to minimize exposure of drugs sensitive to oxidation. Also, the reservoir may keep volatile materials inside the reservoir, for example, to prevent water from evaporating, causing the drug composition to dry out and become undeliverable. For example, the reservoir may be sealed using a topical anesthetic and/or analgesic.

The drug reservoir can be substantially rigid or readily deformable. Typically, the reservoir is a substantially rigid hollow cylinder. The reservoir can be formed from one or more polymers, metals, ceramics, or combinations thereof. In a typical embodiment, the reservoir includes a volume surrounded by one or more walls, or includes a porous material, such as a sponge, which can retain, for example, the drug liquid until the material is compressed.

In aspects, the reservoir is shaped like the barrel of a syringe and optionally mates with a syringe plunger, as described below. It will be understood that the reservoir may be integral with the device or may be removable so that it can be refilled and/or otherwise reused. In aspects, the reservoir may be filled with the drug or composition of choice and then inserted into the device for use. In aspects, the removable reservoir frictionally engages the interior walls of the device and/or mates in any known manner, such as, but not limited to, snap-fitting, press fitting, adhesives, gaskets, and so on.

In certain aspects, the reservoir is formed of an elastic material, such as an elastomeric polymer or rubber. For example, the reservoir can be a balloon-like pouch that is stretched (in tension) when filled with a fluid drug composition to be delivered.

The reservoir of a single microneedle device can include a plurality of compartments that are isolated from one another and/or from a portion of the one or more microneedles in an array. The device can, for example, be provided to deliver different drugs through the same or different needles, or to deliver the same or different drugs at different rates or at different times. Alternatively, the contents of the different compartments can be combined with one another, for example, by piercing, or otherwise removing, a barrier between the compartments, so as to allow the materials to mix. In one aspect, one compartment contains a saline solution or another delivery vehicle, while another compartment contains lyophilized drug. In another aspect, one compartment contains a fast-acting sedative, such as ketamine, and another compartment contains a longer-acting or slower-acting sedative, such as midazolam. In aspects, one or more compartments may contain a drug to reverse the effects of a sedative drug.

In one aspect of the device, the reservoir, as well as other components, are formed from flexible materials to allow the device to fit the contours of the biological barrier, such as the skin, vessel walls, or the eye, to which the device is applied. A flexible device may facilitate more consistent penetration of some biological barriers, because penetration can be limited by deviations in the attachment surface. For example, the surface of human skin is not flat due to dermatoglyphics (i.e. tiny wrinkles) and hair.

One skilled in the art would understand that a rigid reservoir with a curved surface from which the one or more microneedles extend could achieve the same purpose as the aforementioned reservoir made from flexible materials.

Plunger

In certain aspects, the delivery device comprises a plunger to facilitate deformation of the reservoir and expulsion of the pharmacological agent through the microneedles. The plunger itself may be rigid or may be deformable like the reservoir. The plunger may be a separate component or it may simply be an extension of the reservoir. Typically, the plunger is on top of the reservoir, but it will be understood that the plunger could be to a side of the reservoir or it may completely surround the reservoir.

In a typical aspect, the plunger is similar to a typical syringe plunger and is sized to frictionally engage the inner walls of the reservoir, such that when the plunger is depressed it reduces the volume within the reservoir. The plunger may comprise a flexible or deformable gasket, much like the gasket found on a typical syringe, to improve the seal of the plunger with the reservoir and reduce leakage.

One skilled in the art would understand that when the automated delivery of drug and/or deployment of the microneedle is performed (described below), the plunger may be redundant and no longer required to achieve the purpose of the device.

Housing

In typical aspects, the device has a housing that can be constructed from a variety of materials, including, for example, metals, ceramics, and/or polymers. Typically, the housing comprises the reservoir as described herein, an actuator for deploying the microneedle(s) described herein and the plunger as described herein. In aspects, the plunger and the actuator are one in the same. For example, the plunger is the actuator of the device, such as, for example, a syringe type plunger, which, when depressed, results in the depression of the reservoir described herein, and delivery of the drug. In aspects, the plunger and actuator are different. For example, but not limited to, the plunger is like a syringe type plunger and the actuator is a deployable button. In this way, the plunger delivers the drug from the reservoir to the microneedles as described herein and the actuator deploys the one or more microneedles as described herein.

In aspects, the housing further comprises fastening elements as described herein which are suitable for securing the housing to the biological barrier upon which it will be applied. The fastening elements are connected to the housing via connectors which extend laterally from the housing. In aspects, the connectors may be rigidly connected to the housing. In aspects, the connectors may be flexibly connected to the housing. It is contemplated that one of the connectors may be rigidly connected to the housing and the other may be flexibly connected to the housing. One skilled in the art would appreciate that various connections are possible, depending on the requirements of the drug delivery device. The connectors may be made of the same or different material as the housing.

In other aspects, the reservoir is contained within a substantially rigid housing with flexible fastening elements. For example, the band or cuff described herein secures the housing around the arm of the user, allowing for the housing to align with the curvature of the biological barrier (e.g., the skin) upon which it will be applied.

The housing can take on any shape, size and thickness that is suitable for the requirements of the device. For example, the length of the needle required for the procedure would contribute to the overall thickness requirements of the housing described herein. Typically, the thickness of the housing is minimal so as to be concealed by the fastening elements and not bear too much weight on the user's arm while in use. In aspects, the housing is substantially rectangular. In aspects, the housing may have the shape of a square, a circle, or a triangle. One skilled in the art would appreciate that any shape that can support the components described herein for the device to deliver drug transdermally, would be suitable.

Actuation Unit

In some embodiments, the drug delivery device comprises an actuation unit for deployment of the needle from the housing described herein. The actuation unit comprises the actuator described herein, a bottom cap and the microneedle described herein. Typically, the actuation unit is adjacent the reservoir described herein. Together, the actuation unit, the plunger described herein, and the reservoir make up an injection unit of the device. The injection unit is disposed within the housing described herein.

The actuator is a typically a rigid structure with substantially parallel opposing walls, situated within the bottom cap. The bottom cap houses the microneedle of the device described herein. The bottom cap has substantially parallel opposing walls, with at least two indentations along the length thereof. Typically, the at least two indentations are found proximal to a base of the bottom cap (e.g., where the microneedle is ejected).

In aspects, the at least two indentations may individually form a groove through a portion of the substantially parallel opposing walls of the bottom cap. In aspects, the at least two indentations may individually form a complete passage way (e.g., a slit) through the substantially parallel opposing walls of the bottom cap. Typically, a first indentation is upstream of a second indentation along the length of the substantially parallel opposing walls of the bottom cap. Typically, the first and second indentations are substantially adjacent one another along the length of the substantially parallel opposing walls of the bottom cap. One skilled in the art would understand that the position of the first and second indentations is dependent on the length of needle to be ejected from the housing.

The at least two indentations in the substantially parallel opposing walls of the bottom cap are configured for matingly receiving a protuberance extending outwardly from a surface of the substantially parallel opposing walls of the actuator. The protuberance protrudes a sufficient distance to penetrate through the indentations of the bottom cap. This mating relationship provides a frictional engagement between the protuberance of the actuator and the indentation of the bottom cap and can be achieved by any means known in the art, such as, but not limited to, snap-fitting, press fitting and the like. It is contemplated that in embodiments, the substantially parallel walls of the bottom cap have outwardly extending protuberances that are matingly received by indentations on the substantially parallel walls of the actuator.

Typically, the device described herein contains built-in stops and/or a locking mechanism. This is advantageous to the operation of the device in that the stops and/or locking mechanism described herein allows for a pre-determined precise depth of the microneedle penetration into the skin of the patient. Typically, the protuberance of the actuator and the indentation of the bottom cap are aligned with each other in a first reversibly locking position. In this position, the microneedle, described herein, is in an non-deployed state. When the needle is deployed (via engagement of the actuator, such as, but not limited to, depression of a button), the protuberance of the actuator and the indentation of the bottom cap are aligned with each other in a second reversibly locking position.

Advantageously, movement between the first and second reversibly locking positions can produce a sound when the protuberance hits the inner walls of the bottom cap which is useful for altering the user that the needle has been inserted into the skin.

Flange/Adhesive

The drug delivery device, in aspects, comprises a flange upon which an adhesive is applied for securing the device against the biological barrier, such as the skin. The adhesive can be any known adhesive compatible with the biological barrier in question, such as those used in typical bandages. The flange can have any suitable configuration. For example, the flange may surround the entire periphery of the device, or it may be elongated on two sides, such as in a typical bandage.

In aspects, the drug delivery device will be adhered to the skin using a suitable pressure sensitive adhesive. Such an adhesive may include acrylate and/or methacrylate polymers and copolymers, silicones, polyisobutylenes, synthetic rubbers, such as styrene-isoprene-styrene, and mixtures and blends of the foregoing. A particularly beneficial class of adhesives is the class of (meth)acrylate polymers, typically acrylate embodiments thereof, suitable for use as pressure sensitive adhesives (PSAs). Representative examples of such methacrylate PSAs are described in U.S. Pat. Nos. 4,693,776, 4,751,087, 4,737,577, and Re 24,906, each of which is incorporated herein by reference in its entirety.

Fastening Elements

The drug delivery device, in aspects, comprises fastening elements which are suitable for securing the device against the biological barrier, such as the skin. Typically, the fastening elements are connected to the housing described herein by connectors extending outwardly therefrom. In aspects, the fastening elements take the form of a band or a cuff (described below). The band may be in the form of two separate flexible pieces of material that are individually secured to the connectors of the housing described herein. The flexibility of the bands allows the bands to conform to and wrap around the arm of the patient.

Typically, a free end of the band is secured to the other free end of the band using, for example, but not limited to, hook and loop material such as Velcro™, snap fasteners, buttons, and/or adhesive tape applied to one of the bands. In aspects, if the bands are to be secured to each other using an adhesive tape, the portion of the band with the adhesive tape would also typically be covered with a material to prevent the adhesive tape from inadvertently or prematurely sticking to the other band or other items.

In other aspects, the band is in the form of a continuous elastic and/or flexible band, such a sports band, that is attached to the housing using methods known in the art, such as, but not limited to, an adhesive. In other aspects, the band may simply frictionally secure the device against the user's body, such as the patient's arm.

The band, as an elongate piece of material or as two or more separate pieces, may be made of an elastic material which expands in circumference in order to accommodate the dimensions of the patient's arm. Typically, the width and snugness of band is sufficient to engage the patient's arm without sliding up and down or around. The band may be adjustable to fit a variety of sizes and/or may be available in different sizes to fit average arm or leg sizes in patients of different sizes and ages.

In aspects, the band is useful not only for securing the device to the patient's arm, but also for concealing the device from view and distracting the patient before deploying the microneedle(s). The band may be decorated with characters familiar to a child, bright colours, or any other type of ornamentation that will help put the user, such as a child, at ease during the procedure.

In other aspects, the fastening means may be in the form of a cuff configured for both holding and concealing the device from view of the patient and also securing the device to the arm of the patient. The cuff is securable to the arm of the patient using methods understood in the art, for example, but not limited to, Velcro™ hook and loop fasteners or adhesive strips as described herein. In typical embodiments, the device described herein is held by the cuff such that the device is positioned against the skin of the patient for automated deployment of the microneedle(s) as described herein. In aspects, the device described herein is concealed in the cuff or a cuff-like wrapping.

In certain aspects, the cuff resembles a blood pressure cuff, as patients tend to be familiar with such blood pressure cuffs and do not have an inherent fear of such devices. In this way, the cuff disguises the device and mitigates the patient's fear of needles. In such aspects, the cuff may be configured to inflate and collapse and then release pressure about the arm of the patient in a controlled manner and therefore may be considered a dual device that provides for both the measurement of blood pressure before, during, and/or after the micro-injection procedure and provides for the injection procedure itself.

Automated Devices

While manual manipulations of the device have been described herein, it is contemplated that the device described herein can be automated. In aspects, the cuff is attached to a portable base unit for easy automation of the transdermal drug delivery device described herein. In an embodiment, the manual deployment of the actuator and manual transfer of the drug to the microneedle bore from the reservoir is replaced by automated operation of the transdermal drug delivery device.

As described above, the reservoir may be removable and thus allows for a barrel of similar size and shape configurations to be inserted into the drug delivery device and secured therein. One skilled in the art would understand that an outer wall of the barrel would form a frictional fit with an inner wall of the housing, much like that described for the removable reservoir described herein. This frictional fit, may be, but not limited to, snap-fitting, press-fitting and the like.

Typically, the barrel is attached to an end of flexible tubing which is likewise attached, at its other end, to the portable base unit device. A pump in the portable base unit provides a pumping mechanism to move a volume of drug from the barrel to the microneedle bore for subsequent injection into the skin as herein described. In typical aspects, the barrel has a diaphragm that is perforated with the application of air pressure from the pump in the base unit.

Thus, with a push of a button on the portable base unit device, a user, such as, but not limited to, a physician, a clinician and/or a nurse, can transfer the drug automatically (via a pumping mechanism created by the portable base unit) through flexible tubing attached to both the drug delivery device (concealed by the cuff) and the portable base unit. The user can also deploy the microneedle from the device automatically with the press of a button on a portable base unit device. In this way, once the cuff is on the arm of the patient, there is no need to further touch the device in order to deliver the drug transdermally.

In aspects, the flexible tubing connecting the drug delivery device to the portable base unit allows for the drug to be administered to the patient in a titratable fashion. This titration may also be provided by large volume capacity of the barrel which allows for provision/storage of a large volume of drug. For example, the user may add more drug to the drug delivery device via the barrel that is inserted therein, and then pump the drug from the barrel to the microneedle using a pumping action derived from the portable base unit. In another example, more drug than initially thought required can be added to the barrel prior to insertion of the barrel into the drug delivery device and then titrated into the patient. In this way, there is no restriction on the volume of drug available for injection. Thus, for example, a particularly fearful child may be adequately and safely sedated prior to the micro-injection procedure, without requiring disassembly of the cuff and/or drug delivery device and thereby avoiding adding to the anxiety experienced by the child because of the impending procedure.

The portable base unit is similar to a standard blood pressure monitoring device known to those skilled in the art, but instead of (or in addition to) being useful to inflate a blood pressure cuff and monitor blood pressure, the device is capable of delivering drug (described below) to the patient in an automated fashion. In aspects, the portable base unit comprises a main housing, a display panel, on/off (power) and display select switch. The display panel is typically a liquid crystal display (LCD) and may display values for name of drug(s), volume of drug(s), amount of drug(s), time, and so on.

The cuff comprises a sleeve or band securable to the arm of the patient, the microneedle device, and a tubing element connected to the microneedle device to enable the actuation thereof. The microneedle device is operably connected to an actuation and control portion of the portable base unit, which is responsible for exposing the microneedle(s) if they are not already present in the exposed position and pumping the drug from the portable base unit to the microneedle device and into the patient's skin. The cuff can be made of any material suitably used in the art. Typically, the cuff is made of nylon.

Thus, the portable base unit connected to the drug delivery device concealed within the cuff described herein, is useful for distribution of the drug to the user. In the case where the device is a dual device for delivering drug and monitoring blood pressure, one can evaluate the patient's blood pressure prior to, during, and/or after, the micro-injection procedure. This may be desirable for assessing the health of the patient.

Furthermore, as the patient may be familiar with a typical blood pressure cuff, and not afraid thereof, the blood pressure cuff may provide a suitable distraction from the microneedle device described herein. In typical aspects, the cuff itself conceals the microneedle device, or the cuff (containing the microneedle device) can be covered with decorative ornamentation in order to further distract the child from the micro-injection procedure.

Outer Covering

In other aspects, the drug delivery device may be covered with a flexible outer covering that facilitates adhesion or compression of the device against the skin. In typical aspects, the outer covering may disguise the device as a bandage. In this way, a subject will be less likely to fear the device, as bandages will be familiar to the subject and will not typically be a source of anxiety. The outer covering may contain characters familiar to the child, bright colours, or any other type of ornamentation that will help put the subject at ease. The outer covering may alternatively look like a typical plain bandage without any ornamentation.

The outer covering is typically flexible so that it need not be removed in order to compress or deform the reservoir or otherwise actuate the plunger and thereby press the microneedles into the skin and force the drug out of the reservoir, into the microneedles, and into the subject. It will be understood that if the fastening elements described above are used to disguise the device, then the use of an outer covering may be redundant and not included.

In an aspect, the device may be used with slow release drugs and may be designed to slowly self-actuate over a period of several hours to several days. This could be accomplished, for example, by using a flexible outer covering that will slowly contract over the desired period of time, thereby slowly depressing the plunger and delivering the drug.

Drug to be Delivered

The drug delivery device has been described above in the context of delivering one or more sedative or anxiolytic drugs. However, it will be understood that the device can be used to deliver any drug that can be delivered transdermally. For example, the drug delivery device described herein may be used to deliver a drug selected from the group consisting of analgesic agents, anti-arthritic agents; anti-arrhythmic agents; anti-asthmatic agents, anesthetics, anticonvulsants, antidepressants, antibiotics, anticancer agents, antidiabetic agents, anticholinergic antagonists, antidotes, antiviral agents; anti-inflammatory agent, antiglaucoma agents antiemetics, antihistamines, antipanic agents, anti-infective agents, antineoplastics, antiparkisonian drugs, antirheumatic agents, antipsychotics, appetite stimulants, appetite suppressants; attention deficit disorder (ADD) and attention deficit hyperactivity disorder (ADHD) drugs, cholesterol-lowering agents, anxiolytics, appetite stimulants and suppressants, blood modifiers, cardiovascular agents, central nervous system stimulants, drugs for Alzheimer's disease management, drugs for chronic pain, drugs for cystic fibrosis management, diagnostics, dietary supplements, drugs for erectile dysfunction, gastrointestinal agents, hormones, drugs for the treatment of alcoholism, drugs for the treatment of addiction, immunosuppressives, mast cell stabilizers, migraine preparations, motion sickness products, drugs for multiple sclerosis management, muscle relaxants, nonsteroidal anti-inflammatories, opioids, other analgesics and stimulants, opthalmic preparations, osteoporosis preparations, prostaglandins, respiratory agents, sedatives and hypnotics, skin and mucous membrane agents, smoking cessation aids, Tourette's syndrome agents, urinary tract agents, vertigo agents, vaccines, polynucleotides, ribozymes, herbal remedies, nutritional agents, and combinations thereof.

Methods for Manufacture of the Devices

The microneedle and reservoir are made by methods known to those skilled in the art. Examples include microfabrication processes, by creating small mechanical structures in silicon, metal, polymer, and other materials. Three-dimensional arrays of hollow microneedles can be fabricated, for example, using combinations of dry etching processes; micromold creation in lithographically-defined polymers and selective sidewall electroplating; or direct micromolding (Micro-electromechanical systems i.e. MEMS) techniques using epoxy mold transfers. These methods are described, for example, in U.S. Ser. No. 09/095,221, filed Jun. 10, 1998; U.S. Ser. No. 09/316,229, filed May 21, 1999; Henry, et al., "Micromachined Needles for the Transdermal Delivery of Drugs," *Micro Electro Mechanical Systems*, Heidelberg, Germany, pp. 494-98 (Jan. 26-29, 1998). The devices and/or portions thereof may also be made by 3D printing, as would be known to a skilled person.

Methods of Use

The drug delivery devices described herein are typically provided in a ready-to-use format, so that they can be used by a minimally trained person. The devices may be provided pre-dosed, so that a given device will be chosen depending upon the drug of interest and the age and/or weight of the subject. Then, the device can be used by simply opening a sterile package, applying the device like a bandage, or by securing the device via fastening elements, to the biological barrier of choice, typically the upper arm, then depressing the plunger when desired. In aspects, the plunger facilitates movement of the drug between the reservoir and the microneedle bore via connecting tubing. Typically, depression of the plunger results in depression of the reservoir and the drug is delivered to the skin via the microneedle. In other aspects, the device described herein is concealed in a cuff or a cuff-like wrapping allowing for automatic deployment and/or delivery of the drug.

In a typical aspect, the drug delivery device is provided in a sterile package together with a coating of a topical anesthetic and/or analgesic, such as EMLA, covering the microneedles. The package is opened and a cover protecting the adhesive and EMLA may be peeled off. Then, the device is attached gently to the skin using the adhesive without depressing the plunger through the outer covering. After a set period of time sufficient for the EMLA to anesthetize the skin, such as about 10 minutes, for example, the plunger can be depressed to administer the drug.

In other aspects, the device and methods described herein are also used for reversing the sedative drug or for reversing the effect of the sedative drug.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Example 1

The required size for a drug delivery device was calculated for midazolam, administered at 0.3 mg/kg of a 5 mg/ml solution. The diameters for a reservoir with a fixed height of 0.5 cm or 0.3 cm, for children of various ages and weights, are shown in Table 1.

TABLE 1

Midazolam (0.3 mg/kg of 5 mg/ml solution).

| Age (yr) | Weight (kg) | Dose (mg) | Drug volume (ml) | Diameter of reservoir with height of 0.5 cm (cm) | Diameter of reservoir with height of 0.3 cm (cm) |
|---|---|---|---|---|---|
| 1 | 10.0 | 3.00 | 0.600 | 1.2361 | 1.5958 |
| 2 | 12.0 | 3.60 | 0.720 | 1.3541 | 1.7481 |
| 3 | 14.5 | 4.35 | 0.870 | 1.4884 | 1.9216 |
| 4 | 16.5 | 4.95 | 0.990 | 1.5878 | 2.0498 |
| 5 | 18.2 | 5.46 | 1.092 | 1.6676 | 2.1528 |
| 6 | 20.0 | 6.00 | 1.200 | 1.7481 | 2.2568 |
| 7 | 22.5 | 6.75 | 1.350 | 1.8541 | 2.3937 |

Example 2

The required size for a drug delivery device was calculated for midazolam, administered at 0.1 mg/kg of a 5 mg/ml solution together with ketamine, administered at 2.5 mg/kg of a 100 mg/ml solution. The diameters for a reservoir with a fixed height of 0.5 cm, for children of various ages and weights, are shown in Table 2.

TABLE 2

Midazolam (0.1 mg/kg of 5 mg/ml solution) and ketamine (2.5 mg/kg of 100 mg/ml solution).

| Age (yr) | Weight (kg) | Midazolam Dose (mg) | Midazolam volume (ml) | Ketamine Dose (mg) | Ketamine volume (ml) | Total drug volume (ml) | Diameter of reservoir with height of 0.5 cm (cm) |
|---|---|---|---|---|---|---|---|
| 1 | 10.0 | 1.0 | 0.2 | 25.0 | 0.25 | 0.4500 | 1.0705 |
| 2 | 12.0 | 1.2 | 0.24 | 30.0 | 0.3 | 0.5400 | 1.1726 |
| 3 | 14.5 | 1.45 | 0.29 | 36.25 | 0.3625 | 0.6525 | 1.2890 |
| 4 | 16.5 | 1.65 | 0.33 | 41.25 | 0.4125 | 0.7425 | 1.3750 |

TABLE 2-continued

Midazolam (0.1 mg/kg of 5 mg/ml solution) and ketamine (2.5 mg/kg of 100 mg/ml solution).

| Age (yr) | Weight (kg) | Midazolam Dose (mg) | Midazolam volume (ml) | Ketamine Dose (mg) | Ketamine volume (ml) | Total drug volume (ml) | Diameter of reservoir with height of 0.5 cm (cm) |
|---|---|---|---|---|---|---|---|
| 5 | 18.2 | 1.82 | 0.364 | 45.5 | 0.455 | 0.8190 | 1.4441 |
| 6 | 20.0 | 2.0 | 0.4 | 50.0 | 0.5 | 0.9000 | 1.5139 |
| 7 | 22.5 | 2.25 | 0.45 | 56.25 | 0.5625 | 1.0125 | 1.6057 |

Example 3

The required size for a drug delivery device was calculated for dexmedetomidine, administered at 2 mcg/kg of a 100 mcg/ml solution together with ketamine, administered at 2.5 mg/kg of a 100 mg/ml solution. The diameters for a reservoir with a fixed height of 0.5 cm or 0.3 cm, for children of various ages and weights, are shown in Table 3.

TABLE 3

Dexmedetomidine (2 mcg/kg of 100 mcg/ml solution) and ketamine (2.5 mg/kg of 100 mg/ml solution).

| Age (yr) | Weight (kg) | Dexmedetomidine Dose (mg) | Dexmedetomidine volume (ml) | Ketamine Dose (mg) | Ketamine volume (ml) | Total drug volume (ml) | Diameter of reservoir with height of 0.5 cm (cm) |
|---|---|---|---|---|---|---|---|
| 1 | 10.0 | 20.0 | 0.200 | 25.0 | 0.25 | 0.4500 | 1.0705 |
| 2 | 12.0 | 24.0 | 0.240 | 30.0 | 0.3 | 0.5400 | 1.1726 |
| 3 | 14.5 | 29.0 | 0.290 | 36.25 | 0.3625 | 0.6525 | 1.2890 |
| 4 | 16.5 | 33.0 | 0.330 | 41.25 | 0.4125 | 0.7425 | 1.3750 |
| 5 | 18.2 | 36.4 | 0.364 | 45.5 | 0.455 | 0.8190 | 1.4441 |
| 6 | 20.0 | 40.0 | 0.400 | 50.0 | 0.5 | 6.9060 | 1.5139 |
| 7 | 22.5 | 45.0 | 0.450 | 56.25 | 0.5625 | 1.0125 | 1.6057 |

The above disclosure generally describes the present invention. Although specific terms have been employed herein, such terms are intended in a descriptive sense and not for purposes of limitation.

All publications, patents and patent applications cited above are herein incorporated by reference in their entirety to the same extent as if each individual publication, patent or patent application was specifically and individually indicated to be incorporated by reference in its entirety.

Although preferred embodiments of the invention have been described herein in detail, it will be understood by those skilled in the art that variations may be made thereto without departing from the spirit of the invention or the scope of the appended claims.

The invention claimed is:

1. A transdermal drug delivery device comprising:
a reservoir for holding a drug;
at least one microneedle in fluid communication with the reservoir through which the drug can be delivered transdermally;
a housing surrounding the reservoir;
a fastening element configured to conceal the housing from view during operation thereof;
an injection unit housed within the housing, wherein the injection unit comprises a bottom cap; and
an actuator for deploying the at least one microneedle, wherein the bottom cap comprises a first indentation or void with a first positon and a second indentation or void with a second position relative to the first position and wherein the first indentation or void lockingly engages one of a pair of protuberances on the actuator before actuation of the at least one microneedle and the second indentation or void locking engages with one of the pair of protuberances on the actuator after actuation of the at least one microneedle.

2. The transdermal drug delivery device of claim 1, wherein the reservoir is rigid.

3. The transdermal drug delivery device of claim 1, further comprising a plunger for delivering the drug from the reservoir through the at least one microneedle.

4. The transdermal delivery device of claim 1, wherein the at least one microneedle is one microneedle.

5. The transdermal delivery device of claim 1, wherein the fastening element is attachable to the housing, configured for securing the transdermal delivery device to a wearer, and comprises ornamentation selected so as to appeal to a child.

6. The transdermal delivery device of claim 1, further comprising connecting tubing in fluid communication with the reservoir and the at least one microneedle.

7. The transdermal delivery device of claim 1, wherein device is remotely operable and operably coupled to a portable base unit for delivering the drug and/or deploying the at least one microneedle.

8. The transdermal delivery device of claim 1, wherein the device is automated.

9. The transdermal drug delivery device of claim 1, comprising more than one reservoir.

10. The transdermal delivery device of claim 1, wherein movement of the pair of protuberances before and after actuation alerts a user that the at least one microneedle has been ejected from the housing.

11. The transdermal delivery device of claim 1, wherein the bottom cap has a trough for application for a topical anesthetic and/or analgesic.

12. A method of delivering a drug transdermally, the method comprising expelling a drug from the reservoir of the transdermal drug delivery device of claim 1 through the at least one microneedle and into the skin of a subject.

13. The method of claim 12, for sedating a subject.
14. The method of claim 12, wherein the subject is a child.

* * * * *